(12) United States Patent
Peine et al.

(10) Patent No.: US 12,064,877 B2
(45) Date of Patent: Aug. 20, 2024

(54) INPUT SHAPER FOR ROBOTIC SURGICAL SYSTEM

(71) Applicant: Covidien LP, Mansfield, MA (US)

(72) Inventors: William J. Peine, Ashland, MA (US); Stefan Joerg, Munich (DE); Paul M. Loschak, Somerville, MA (US); Reuben Hale, Oakland, CA (US); Campbell M. Dixon, Oakland, CA (US)

(73) Assignee: Covidien LP, Mansfield, MA (US)

( * ) Notice: Subject to any disclaimer, the term of this patent is extended or adjusted under 35 U.S.C. 154(b) by 389 days.

(21) Appl. No.: 17/430,118

(22) PCT Filed: Jun. 5, 2019

(86) PCT No.: PCT/US2019/035516
§ 371 (c)(1),
(2) Date: Aug. 11, 2021

(87) PCT Pub. No.: WO2020/171836
PCT Pub. Date: Aug. 27, 2020

(65) Prior Publication Data
US 2022/0134555 A1 May 5, 2022

Related U.S. Application Data

(60) Provisional application No. 62/809,209, filed on Feb. 22, 2019.

(51) Int. Cl.
*B25J 9/16* (2006.01)
*A61B 34/30* (2016.01)
(Continued)

(52) U.S. Cl.
CPC ............. *B25J 9/1653* (2013.01); *A61B 34/30* (2016.02); *B25J 9/12* (2013.01); *B25J 15/0019* (2013.01);
(Continued)

(58) Field of Classification Search
CPC ........ B25J 9/1653; B25J 9/12; B25J 15/0019; B25J 9/1635; B25J 9/1689; A61B 34/30;
(Continued)

(56) References Cited

U.S. PATENT DOCUMENTS 8,828,023 B2 9/2014 Neff et al.
2011/0264108 A1 10/2011 Nowlin et al.
(Continued)

FOREIGN PATENT DOCUMENTS

JP 2000099126 A 4/2000
JP 2014164498 A 9/2014
(Continued)

OTHER PUBLICATIONS

International Search Report mailed Nov. 25, 2019 and Written Opinion completed Nov. 15, 2019 corresponding to counterpart Int'l Patent Application PCT/US2019/035516.
(Continued)

*Primary Examiner* — Jason Holloway
(74) *Attorney, Agent, or Firm* — Carter, DeLuca & Farrell LLP

(57) ABSTRACT

Input shapers for control inputs to the robotic surgical system and their method of controlling a linkage of a robot with a controller includes receiving a desired joint angle of a joint of the robot; and transmitting a first control signal to a motor to actuate the joint in response to a desired joint velocity, the desired joint velocity being a function of the desired joint angle and a current joint angle of the joint.

18 Claims, 16 Drawing Sheets

(51) Int. Cl.
*B25J 9/12* (2006.01)
*B25J 15/00* (2006.01)

(52) U.S. Cl.
CPC .............. *G05B 2219/34013* (2013.01); *G05B 2219/39195* (2013.01)

(58) Field of Classification Search
CPC ........... A61B 2017/00017; A61B 2017/00154; A61B 2034/2048; A61B 2034/2059; A61B 2090/067; A61B 2090/371; A61B 2090/373; A61B 2090/376; A61B 2090/378; A61B 34/37; G05B 2219/34013; G05B 2219/39195; G05B 2219/41217
See application file for complete search history.

(56) References Cited

U.S. PATENT DOCUMENTS

| | | |
|---|---|---|
| 2014/0039678 A1 | 2/2014 | Motoyoshi |
| 2014/0039681 A1 | 2/2014 | Bowling et al. |
| 2014/0052154 A1* | 2/2014 | Griffiths ................. A61B 34/30 606/130 |
| 2015/0190928 A1* | 7/2015 | Motoyoshi ............. B25J 9/1694 700/258 |
| 2017/0071680 A1 | 3/2017 | Swarup et al. |
| 2021/0162598 A1* | 6/2021 | Groth ..................... B25J 9/1651 |
| 2021/0212777 A1 | 7/2021 | Cheng |

FOREIGN PATENT DOCUMENTS

| | | |
|---|---|---|
| JP | 6043944 B2 | 12/2016 |
| JP | 2017513549 A | 6/2017 |
| JP | 2019012458 A | 1/2019 |
| KR | 10-2000-0055004 A | 9/2000 |
| WO | 2019012040 A1 | 1/2019 |
| WO | 2020163263 A1 | 8/2020 |

OTHER PUBLICATIONS

Extended European Search Report dated Oct. 26, 2022 corresponding to counterpart Patent Application EP 19916150.6.
Office Action dated May 19, 2023 for Japanese Patent Application No. 2021-549272 (16 pages).
Office Action issued in corresponding Canadian Application No. 3,129,060 dated Feb. 23, 2024 (5 pages).

* cited by examiner

SECOND ORDER SYSTEM WITH $\zeta = 0.1$ AND $\omega_d = 2\pi \times 5$ Hz

SECOND ORDER SYSTEM WITH $\zeta = 0.1$ AND $\omega_d = 2\pi \times 3$ Hz

SECOND ORDER SYSTEM WITH $\zeta = 0.02$ AND $\omega_d = 2\pi \times 5$ Hz

INPUT SHAPER FOR ROBOTIC SURGICAL SYSTEM

CROSS-REFERENCE TO RELATED APPLICATIONS

The present application is a U.S. National Stage Application filed under 35 U.S.C. § 371(a) claiming the benefit of and priority to International Patent Application No. PCT/US2019/035516, filed Jun. 5, 2019, which claims the benefit of and priority to U.S. Provisional Patent Application Ser. No. 62/809,209, filed Feb. 22, 2019, the entire disclosures of each of which being incorporated by reference herein.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector of a surgical instrument that acts on a patient. The user interface includes an input controller or handle that is moveable by the surgeon to control the robotic surgical system and a display allowing the surgeon to visualize the surgical instrument within a surgical site.

The surgical instrument is supported by an arm of a surgical robot. The arm of the surgical robot includes a setup arm and a linkage that are movable within the surgical environment to manipulate the surgical instrument. The linkage is supported by the setup arm and supports the surgical instrument within the surgical environment. The setup arm may move during the surgical procedure to reposition the linkage and/or to avoid collisions with other arms of the surgical robot.

There is a need for determining the position and/or pose of the setup arm within the surgical environment to determine the position of the surgical instrument and thus, control the surgical instrument during a surgical procedure. Thus, there is a continuing need for determining the pose of the setup arm within the surgical environment during a surgical procedure.

SUMMARY

This disclosure relates generally to robotic surgical systems, and more particularly to input shapers for control inputs to the robotic surgical system and their method of processing.

In an aspect of the present disclosure, a method of controlling a linkage of a robot with a controller is provided and includes receiving a desired joint angle of a joint of the robot; and transmitting a first control signal to a motor to actuate the joint in response to a desired joint velocity, the desired joint velocity being a function of the desired joint angle and a current joint angle of the joint.

Transmitting the first control signal may include generating the first control signal as a function of a sum of a current joint angle of the joint and a product of the desired joint velocity and a unit of time, wherein the unit of time is a servo rate of the motor.

The method may include generating the desired joint velocity by calculating a phase shift of the joint based on a resonant frequency of the joint.

The method may further include determining the resonant frequency of the joint based on a current joint angle.

Determining the resonant frequency of the joint may include calculating the resonant frequency based on a frequency map of the linkage.

The method may further include transmitting a second control signal to the motor to actuate the joint in response to the desired joint angle. The second control signal may include a delayed pulse as a remainder of the desired joint velocity not included in the first control signal.

The method according to claim 6, wherein transmitting the second control signal occurs when a phase is less than 180 degrees.

Generating the desired joint velocity may include setting a servo rate of the motor and integrating the desired joint velocity at the servo rate of the motor. The method may further include setting the servo rate of the motor in a range of 0.5 KHz to 2 KHz.

Generating the desired joint velocity may include applying a phase look ahead algorithm to the first control signal.

The method may further include generating a frequency map of the linkage before receiving the desired joint angle. The frequency map may include a resonant frequency of the first joint and each other joint of the linkage in a plurality of poses of the linkage.

Transmitting the first control signal may shape the desired joint velocity in a first mode of vibration. Transmitting the first control signal may shape the desired joint velocity in a second mode of vibration.

According to another aspect of the present disclosure, a surgical robot is provided and includes a linkage configured to support a tool, the linkage having a joint; a motor operably coupled to the joint and configured to actuate the joint to vary a joint angle of the joint; and a controller configured to receive a desired joint angle of the joint; and transmit a first control signal to the motor to actuate the joint in response to a desired joint velocity, the desired joint velocity being a function of the desired joint angle and a current joint angle of the joint.

The controller may be configured to determine the resonant frequency of the joint based on a current joint angle.

Determining the resonant frequency of the joint may include calculating the resonant frequency based on a frequency map of the linkage.

According to a further aspect of the present disclosure, a robotic surgical system is provided and includes a user interface configured to receive input from a user and to transmit an input signal; and a surgical robot. The surgical robot includes a linkage configured to support a tool, the linkage having a joint; a motor operably coupled to the joint and configured to actuate the joint to vary a joint angle of the joint; and a controller configured to receive the input signal including a desired joint angle of the joint; and transmit a first control signal to the motor to actuate the joint in response to a desired joint velocity, the desired joint velocity being a function of the desired joint angle and a current joint angle of the joint.

The controller may be configured to determine the resonant frequency of the joint based on a current joint angle.

Determining the resonant frequency of the joint may include calculating the resonant frequency based on a frequency map of the linkage.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
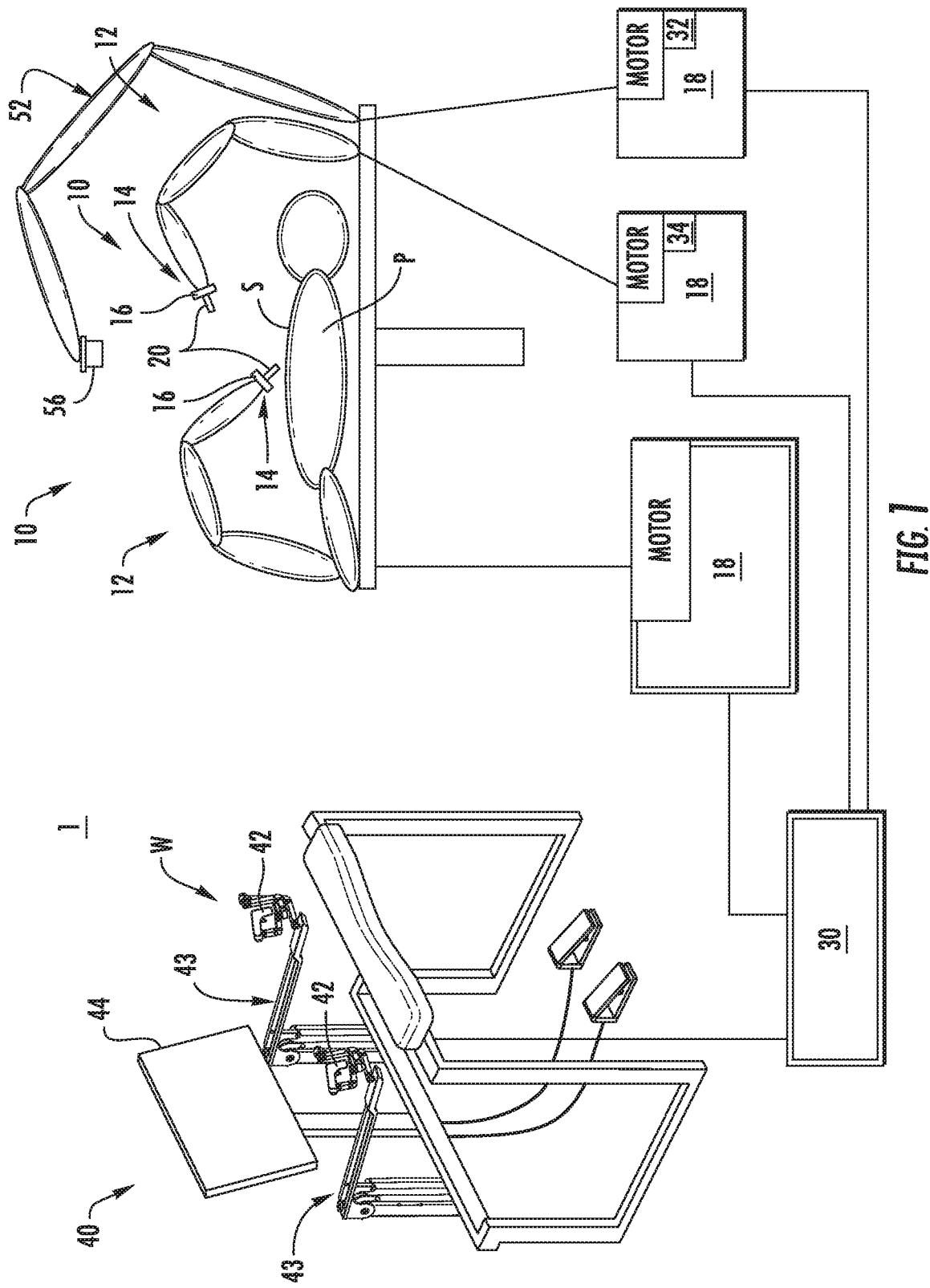
FIG. 1 is a schematic of an exemplary robotic surgical system provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel.

Referring to FIG. 1, a robotic surgical system 1 in accordance with the present disclosure is shown generally as a surgical robot 10, a processing unit 30, and a user console 40. The surgical robot 10 generally includes linkages or arms 12 and one or more robot bases 18 that each support one of the linkages 12. The linkages 12 moveably support an end effector or tool 20 which is configured to act on tissue. The linkages 12 each have an end 14 that supports the end effector or tool 20 which is configured to act on tissue. In addition, the ends 14 of the linkages 12 may include an imaging device 16 for imaging a surgical site "S". The user console 40 is in communication with the robot bases 18 through the processing unit 30. In addition, the robot bases may each include a controller 32, 34 that is in communication with the processing unit 30.

The user console 40 includes a display device 44 which is configured to display three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user console 40 also includes input handles 42 which are supported on control arms 43 which allow a clinician to manipulate the surgical robot 10 (e.g., move the linkages 12, the ends 14 of the linkages 12, and/or the tools 20). Each of the input handles 42 is in communication with the processing unit 30 to transmit control signals thereto and to receive feedback signals therefrom. Additionally or alternatively, each of the input handles 42 may include input devices (not explicitly shown) which allow the surgeon to manipulate (e.g., clamp, grasp, fire, open, close, rotate, thrust, slice, etc.) the tools 20 supported at the ends 14 of the linkages 12.

Each of the input handles 42 is moveable through a predefined workspace to move the ends 14 of the linkages 12, e.g., tools 20, within a surgical site "S". The three-dimensional images on the display device 44 are orientated such that the movement of the input handles 42 moves the ends 14 of the linkages 12 as viewed on the display device 44. The three-dimensional images remain stationary while movement of the input handles 42 is scaled to movement of the ends 14 of the linkages 12 within the three-dimensional images. To maintain an orientation of the three-dimensional images, kinematic mapping of the input handles 42 is based on a camera orientation relative to an orientation of the ends 14 of the linkages 12. The orientation of the three-dimensional images on the display device 44 may be mirrored or rotated relative to the view captured by the imaging devices 16, 56. In addition, the size of the three-dimensional images on the display device 44 may be scaled to be larger or smaller than the actual structures of the surgical site permitting a clinician to have a better view of structures within the surgical site "S". As the input handles 42 are moved, the tools 20 are moved within the surgical site "S" as detailed below. Movement of the tools 20 may also include movement of the ends 14 of the linkages 12 which support the tools 20.

For a detailed discussion of the construction and operation of a robotic surgical system 1, reference may be made to U.S. Pat. No. 8,828,023, the entire contents of which are incorporated herein by reference.

Figure 2:
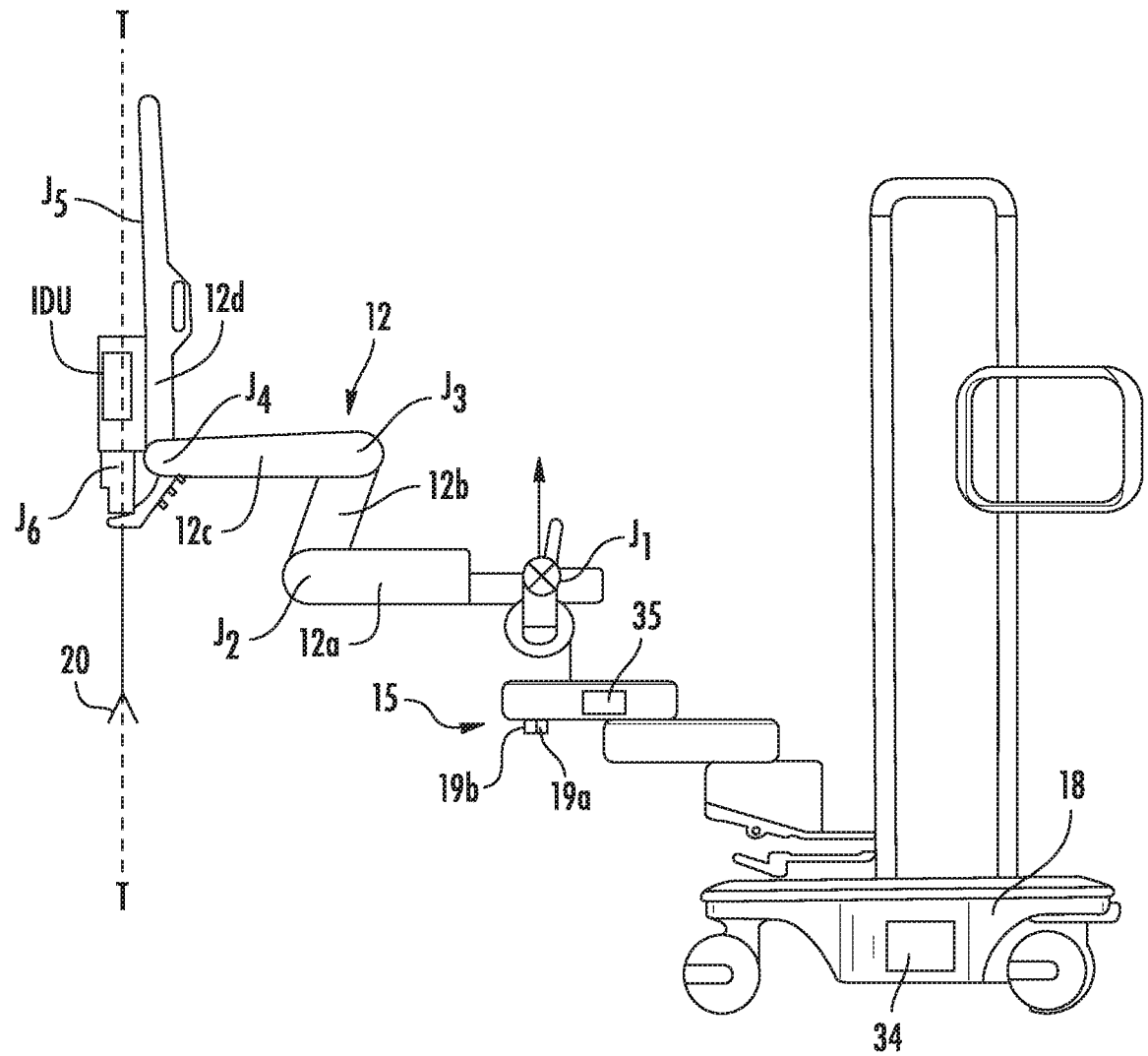
FIG. 2 is a side view of a robot base or cart of a surgical robot of the robotic surgical system of FIG. 1.

Referring to FIG. 2, the surgical robot 10, shown as a robot base or cart 18, includes a setup arm 15 that supports a first portion of a first link 12a of the linkage 12 at a first joint $J_1$ such the first link 12a is substantially parallel to the floor. The first joint $J_1$ is a single degree of freedom joint which allows the first link 12a to rotate about the first joint about an axis that is substantially orthogonal to the floor. The robot base 18 also includes a brake 19 that has an engaged configuration in which the brake 19 prevents movement of the setup arm 15 and a disengaged or released configuration in which movement of the setup arm 15 is permitted.

Forward or inverse kinematics may be used to control the position of the tool 20. In addition, the hand-eye coordination calculations may be used to control the position of the tool 20. For a detailed discussion of exemplary kinematic control algorithms, reference can be made to U.S. patent application Ser. No. 16/081,773, filed Aug. 31, 2018, and for a detailed discussion of exemplary hand-eye coordination calculation reference can be made to U.S. Provisional Patent Application Ser. No. 62/801,734, filed Feb. 6, 2019. The entire contents of each of the above applications are hereby incorporated by reference.

With continued reference to FIG. 2, the linkage 12 includes the first link 12a, a second link 12b, a third link 12c, and a fourth link or rail 12d. Each link is pivotally coupled to at least one other link about a single degree of freedom joint as detailed below. The second link 12b includes a first portion that is pivotally coupled to a second portion of the first link 12a by a second joint $J_2$ and a first portion of the third link 12c is pivotally coupled to a second portion of the second link by a third joint $J_3$. The second and third links 12b, 12c are pivotal about axes of the second and third joints $J_2$, $J_3$ that are parallel to one another and perpendicular to the axis of the first joint $J_1$. In embodiments, movement of the second and third links 12b, 12c about the second and third joints $J_2$, $J_3$ is linked such that movement of the second link 12b about the second joint $J_2$ is equal and opposite to movement of the third link 12c about the third joint $J_3$ such that the third link 12c remains parallel to the first link 12b. The fourth link 12d is coupled to a second portion of the third link 12c about a fourth joint $J_4$. Movement of the fourth link 12d about the fourth joint $J_4$ is about an axis parallel to the axes of the second and third joints $J_2$, $J_3$.

The linkage 12 includes an instrument drive unit (IDU) that is slidably supported along the fourth link 12d to define a linear fifth joint $J_5$ which allows the IDU to move along a tool axis T-T that is parallel to a longitudinal axis of the fourth link 12d. A sixth joint $J_6$ is a roll joint of the IDU about the tool axis T-T which permits the IDU, and thus the tool 20, to rotate about the tool axis T-T.

One or more of the joints $J_1$-$J_6$ may include sensors to determine the position or joint angles of the respective joint. For example, the first joint $J_1$ includes a first sensor 112 that is configured to determine the position of the first link 12a relative to the setup arm 15 about the first joint $J_1$. The second joint $J_2$ includes a second sensor 114 that is configured to determine the position of the second link 12b relative to the first link 12a about the second joint $J_2$. The fifth joint $J_5$ includes a third sensor 116 that is configured to determine the position of the IDU along the rail 12d. The sixth joint $J_6$ includes a fourth sensor 118 that is configured to determine a roll of the IDU about the tool axis T-T. In embodiments, the first, second, third, and fourth sensors 112, 114, 116, 118 may be encoders or potentiometers which determine the joint angle of the respective joint $J_1$, $J_2$, $J_5$, $J_6$. In addition, the IDU may include an inertial measurement unit (IMU) 120 that is configured to determine the inertia of the IDU, e.g., to determine the gravitational forces on the IDU.

The robot base 18 includes the controller 34 and an arm drive unit (ADU) 35 that includes one or more motors. The controller 34 is in communication with the processing unit 30 and is configured to provide control signals to the ADU 35 to control movement of the linkage 12 in response to input signals provided by the processing unit 30 from the user console 40.

The ADU 35 or the controller 34 includes an input shaper algorithm that shapes the desired position input signal commands from the user console 40 to reduce vibrations due to resonant modes of the linkage 12. The resulting motion of the linkage 12 may be smoothed to allow for more dexterous control of the linkage 12 with higher accuracy.

While the input shaper algorithm is described for use with and optimized for use with teleoperated robotic surgical systems, the input shaper algorithm can be used with any motion-controlled mechanism. Specifically, the algorithm is optimized for systems that are driven by a human operator and/or do not follow a predefined path. This means that vibration reduction must be accomplished in real-time as the motion commands are generated. Traditional smoothing algorithms could be used; however, traditional smoothing algorithms tend to introduce significant latency in the motion due to the required number of samples needed to filter out lower frequency modes of vibration. In contrast, the input shaper algorithm described herein reduces vibrations with minimal latency.

Figure 3:
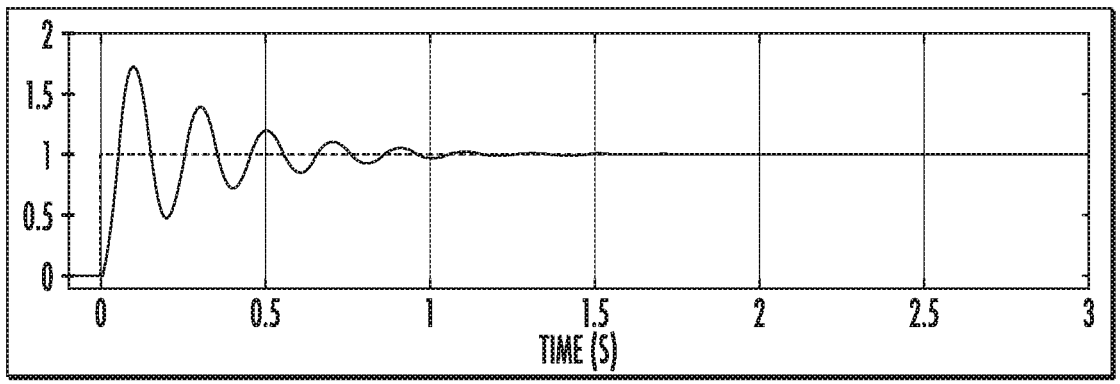
FIG. 3 are prior art graphs showing the response to a unit step of three second order systems having a varying dampening ratios and resonant frequencies FIG. 4 are graphs illustrating principles of a prior art two-step input shaper algorithm.
Figure 3:
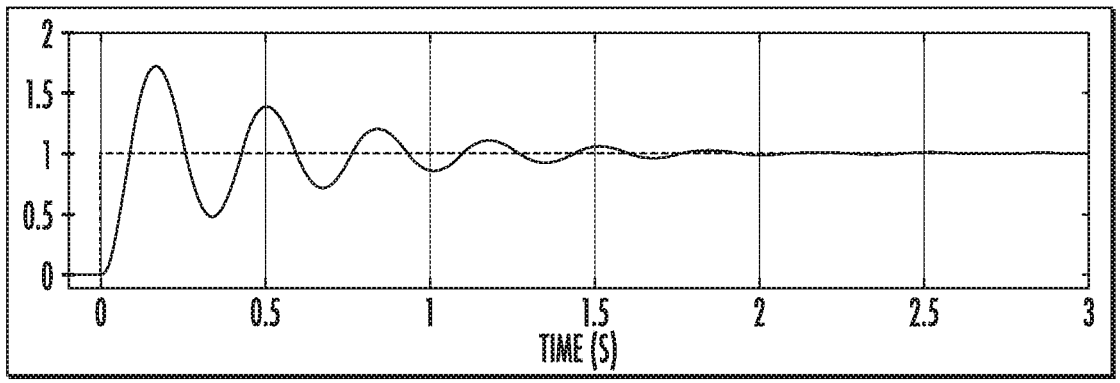
Figure 3:
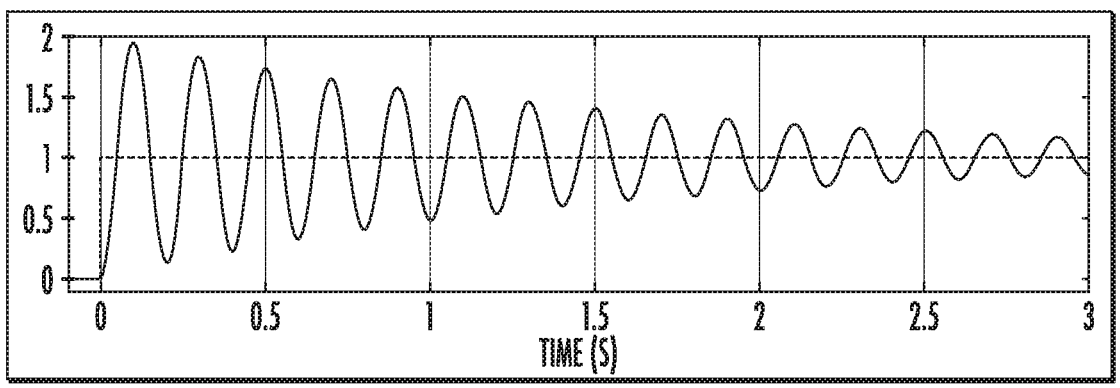
Figure 4:
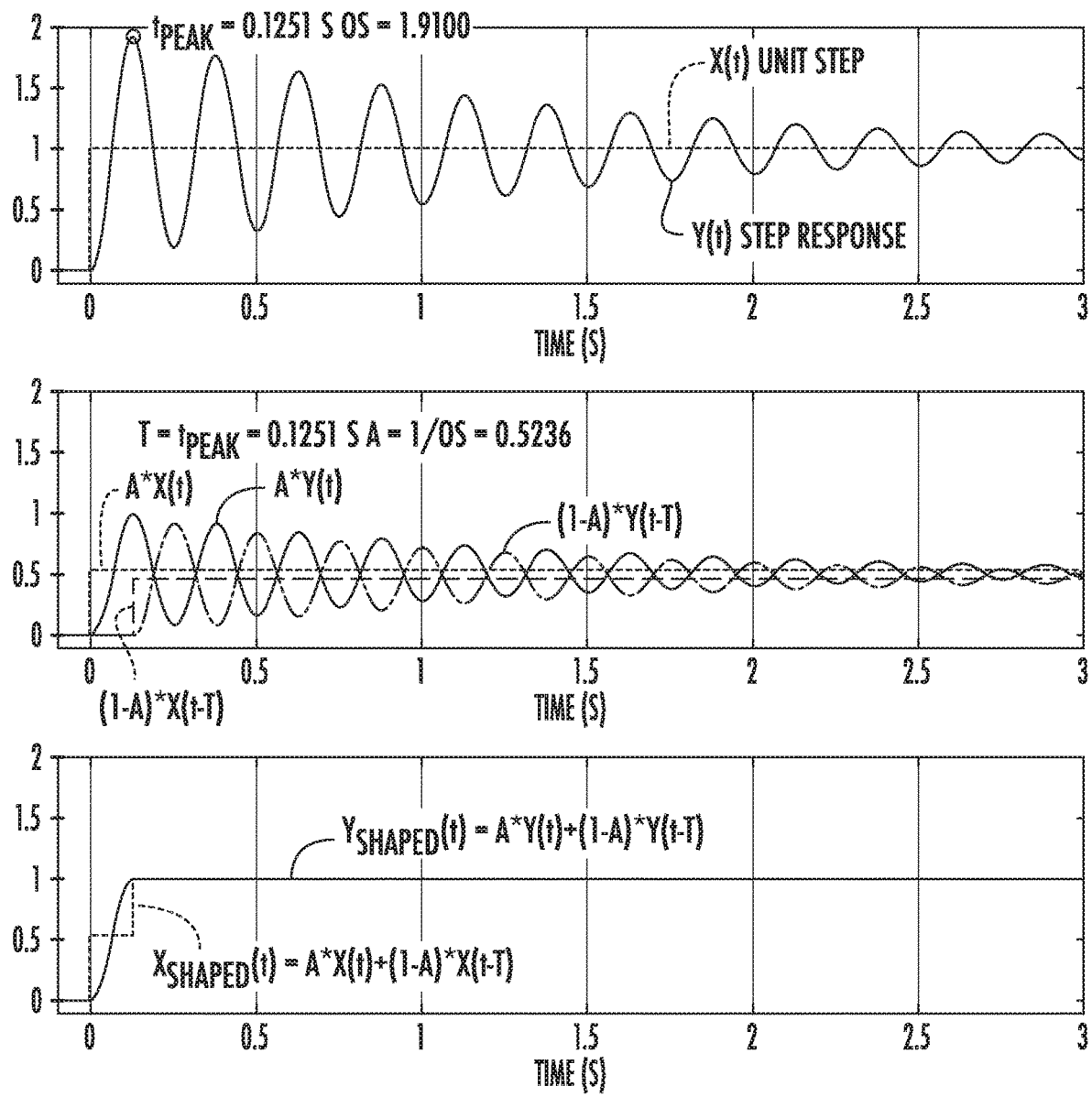

With reference to FIGS. 3 and 4, a prior art two-step input shaper algorithm is detailed to illustrate the advantages of the improved input shaper algorithms detailed herein. As shown in FIG. 3, an underdamped $2^{nd}$ order system is shown after a unit step response of a system, e.g., the movement of a linkage 12. As a result of the step movement from 0 to 1 at a time of 0, the system will overshoot the movement and then oscillate until settling at the desired position of 1 after a ring down time. As shown, a magnitude of the overshoot and the length of time of the ring down time vary as a result of a damping ratio $\zeta$ and the damped resonant frequency $\omega_d$. In addition, the frequency of the oscillations is proportional to damped resonant frequency $\omega_d$ and smaller values of the damping ratio $\zeta$ cause a large magnitude of the overshoot and a longer ring down time.

The prior art two-step input shaper algorithm works by allowing part of the input signal A to go through at normal speed without any time delay and then sending the remainder of the input signal (1-A) through a specific time delay T where A and T are chosen based on a magnitude of the overshoot and a time of the first peak of the unit step response. The shaped signal is provided by the following:

$$X_{shaped}(t) = A*X(t) + (1-A)*X(t-T)$$

where A=1/OS and T=$t_{peak}$.

As shown in FIG. 4, the prior art two-step input shaper algorithm is shown with the top graph showing the undamped result of a unit step input X(t) and the resulting step response Y(t). The circle shows the $t_{peak}$ and the magnitude of the OS without the prior art two-step input shaper algorithm. With particular reference to the middle graph of FIG. 4, part of the input signal A allowed to go through at normal speed is selected such that the overshoot of the first step results in the peak being equal to the unit step and occurs at $t_{peak}$. The remainder of the input signal (1-A) is then sent through starting at $t_{peak}$ such that the oscillations are canceled which result in the total movement as shown in the bottom graph of movement to the unit and then a cancelation of the oscillations which results in the movement $Y_{shaped}(t)$. In this example, the prior art two-step input shaper algorithm completely removes the oscillations in the shaped output signal $Y_{shaped}(t)$ by delaying the second part of the single to be perfectly out of phase with the original signal which results in the sum of the signals canceling the oscillations.

The prior art two-step input shaper algorithm works if the resonant frequency and the dampening of the system remains constant. However, in many systems, e.g., robotic arm 12, the resonant frequency of the system may be dependent on the configuration or the pose of the system. For example, the resonant frequency of linkage 12 may be higher when the arm is folded up near base 18 (FIG. 2) when compared to the resonant frequency when the linkage 12 is stretched out. In addition, a mass of a load at the end of a system, e.g., at the tool 20, may also affect the resonant frequency.

Figure 5:
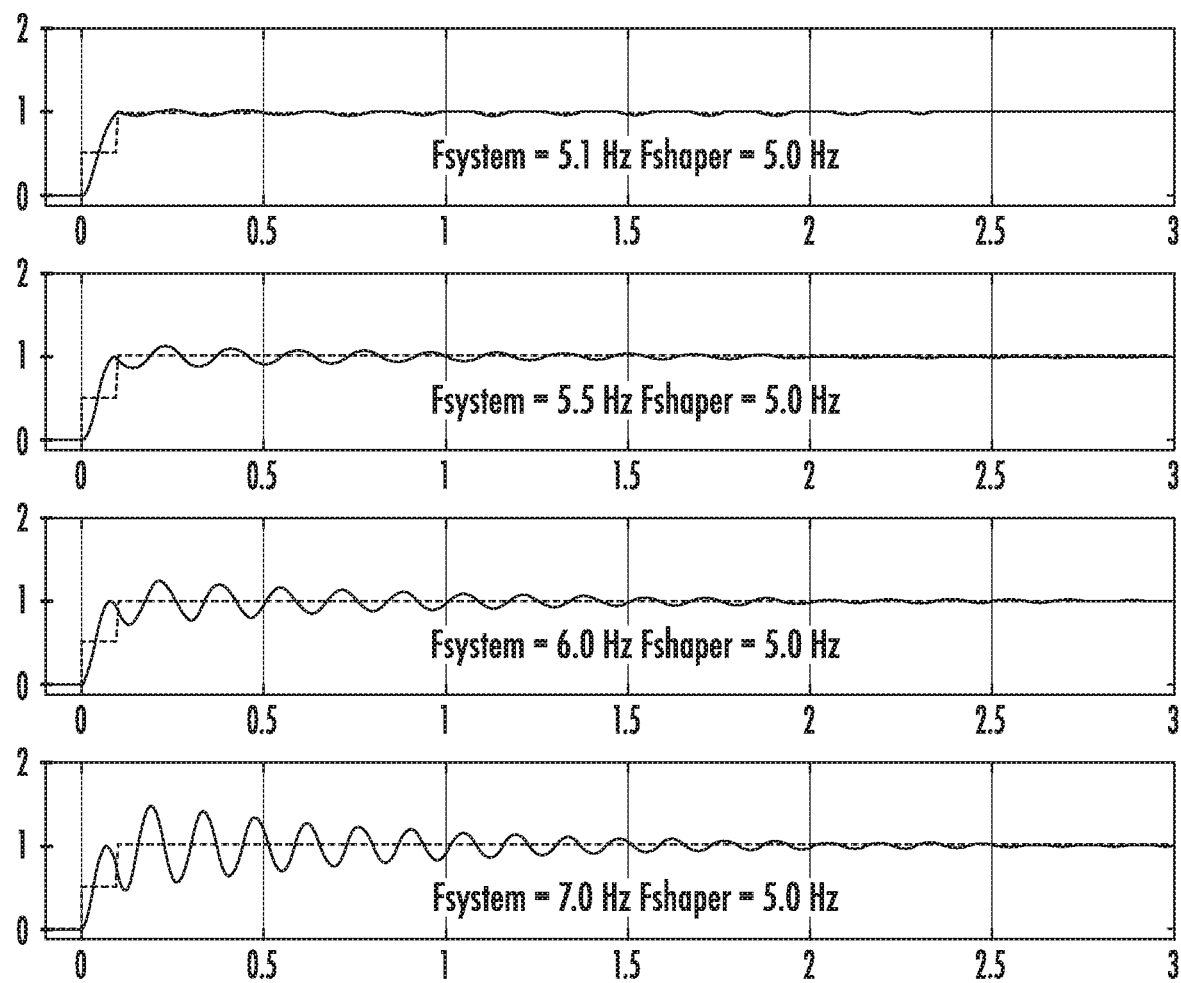
FIG. 5 are graphs illustrating the output of the prior art two-step input shaper algorithm applied to systems with increasing resonant frequencies.
Figure 6:
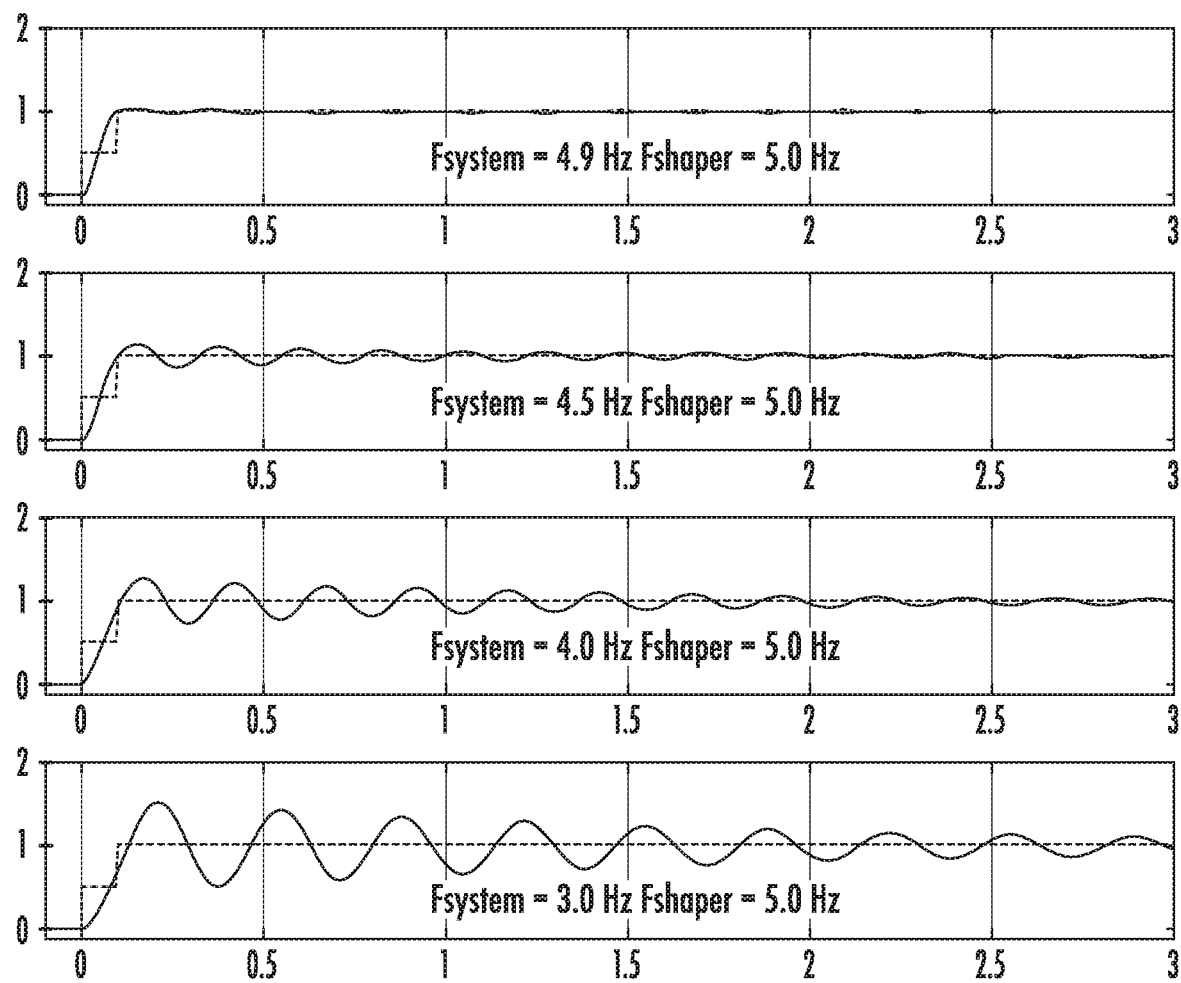
FIG. 6 are graphs illustrating the output of the prior art two-step input shaper algorithm applied to systems with decreasing resonant frequencies.

With particular reference to FIGS. 5 and 6, if the resonant frequency and/or the dampening of the system vary, the amount of residual vibration will increase as the discrepancy between the resonant frequency and the damping of the system and the input shaper increases. For example, as shown in FIG. 5, when the resonant frequency of the system increases the overshoot increases and the ring down time increases. Similar, as shown in FIG. 6, when the resonant frequency of the system decrease, the overshoot increases and the ring down time increases. Thus, it is desirable to create an input shaper that is not affected by changes in the resonant frequency of the system or that can adapter to changes in the resonant frequency of the system.

One method that has been used to address systems with varying resonant frequency and/or dampening is to use a prior art three-step input shaper algorithm. A prior art three-step input shaper algorithm is similar to the prior art two-step input shaper algorithm detailed above but uses two delayed copies of the original signal such that $$X_{shaped}(t)=A*X(t)+B*X(t-T)+C*X(t-2*T)$$

where $A+B+C=1$. While this prior art three-step input shaper algorithm is more resilient to changes in resonant frequency the prior art three-step input shaper algorithm adds additional latency in the commanded signals, roughly double the latency of the prior art two-step input shaper algorithm, which may be undesirable. For example, in teleoperative surgical systems, e.g., robotic surgical system 1, latency of system should be minimized, e.g., less than 100 ms. This can be difficult to achieve with prior art three-step input shaper algorithm when the resonant frequency produces vibrations that are less than 10 Hz. Thus, there is a need for an input shaper algorithm that is resilient to changes in frequency on par or better than a prior art three-step input shaper algorithm that has latency on par or better than the prior art two-step input shaper algorithm.

A first improved input shaping algorithm in accordance with the present disclosure compensates for a changing resonant frequency by changing the time delay T and weighting the magnitude of the overshoot A in real-time (e.g., on the fly) and is described with reference to the linkage 12 of FIG. 2. Specifically, the time delay T and the damping ratio can be made to be functions of the joint angles of one or more of the joints of the linkage 12. The first improved input shaping algorithm may provide a lower latency than the two-point prior art input shaping algorithm and also for improved vibration suppression when the resonant frequency varies.

The functions of time delay T and damping ratio can be determined by creating a frequency map for each joint of the arm 12. The frequency map can be created by setting each joint in a known position or pose and then inducing motion of that joint at the known pose and determining the $t_{peak}$ and overshoot A for the known pose. Once a frequency map is created for each joint, a one-dimensional input shaper for each joint using the prior art two-step input shaper algorithm using the values of taken from the frequency map can be used to create the first improved input shaper algorithm. In embodiments, the frequency map may be can be applied to Cartesian space of the pose of the robot or can be applied to each joint individually.

A second improved input shaper algorithm or velocity input shaper algorithm in accordance with the present disclosure compensates for a changing resonant frequency with a fixed vibration frequency in discrete time as part of a controller, e.g., ADU 35, where desired positions are updated at a set interval. The second improved input shaper algorithm uses the following equation:

$$X_{shaped}[m]=A*X[m]+(1-A)*X[m-\text{floor}(T/dt)]$$

where X is an array of desired joint angles, m is the current index count, A is the magnitude of the overshoot, T is the time of $t_{peak}$, and dt is the time interval between servo cycles of the controller. To utilize this equation, A and T are made into functions of the current joint angles; however, there may be times when the integer value of floor(T/dt) may skip a value or keep the same value for consecutive servo cycles of the controller. Discontinuities may occur in the desired joint commands when there is skipping or repeating of the same value which are not acceptable for smooth motion. To resolve this, the second improved input shaper algorithm applies the desired joint commands to the desired joint velocity instead of the desired joint position by using the following:

$$V[m]=X[m]-X[m-1]$$

$$V_{shaped}[m]=A*V[m]+(1-A)*V[m-\text{floor}(T/dt)]$$

$$X_{shaped}[m]=X_{shaped}[m-1]+V_{shaped}[m]*dt$$

While there may still be discontinuities in the desired velocity of the joints, this can be minimized by utilizing a high servo rate of the controller such that dt is small. In certain instances, it may also be possible to apply an improved input shaper algorithm to an acceleration signal and double integrate to obtain position. Using the acceleration data may further smooth the position commands but comes at a cost of using with the increased noise of acceleration data created by double differentiating the original desired position signals.

Figure 7:
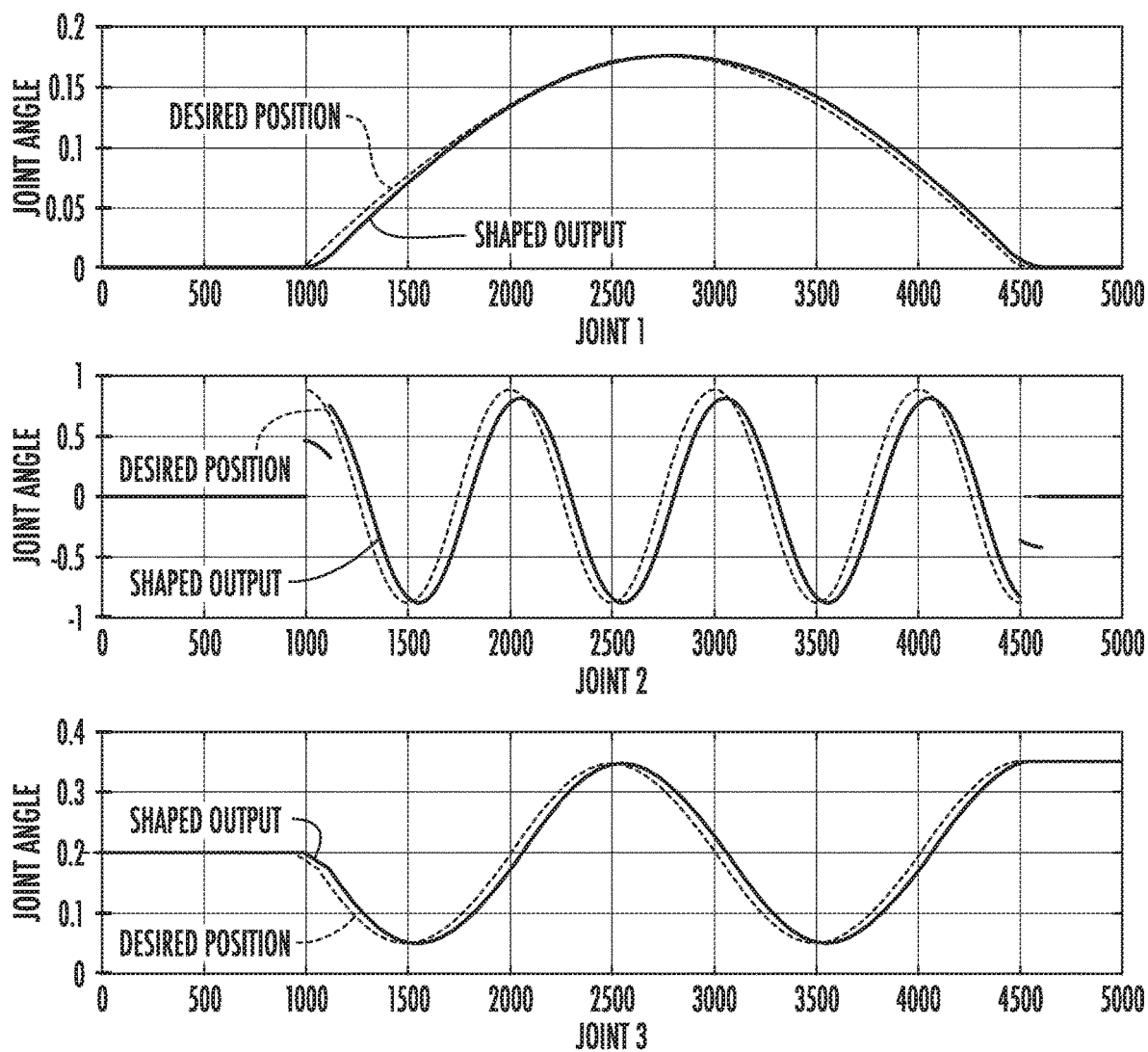
FIG. 7 are graphs of a desired position vs. a shaped position of three joints of the robot base of FIG. 2 when processed through a velocity based input shaper algorithm provided in accordance with the present disclosure.

With reference to FIG. 7, the tracking of joint angle of the three joints of a 3 DOF robot arm, e.g., linkage 12 (FIG. 2). As most clearly seen in the middle graph, the second improved input shaper algorithm has a time delay when the desired position is discontinuous at the start and the end of a motion. This also shows that the time delay at the beginning of the move, near sample 1000, is greater than the time delay at the end of the move, near sample 4500, which is the result of the resonant frequency being lower when this joint is stretched out at the end of the move when compared to the beginning of the move.

Figure 8:
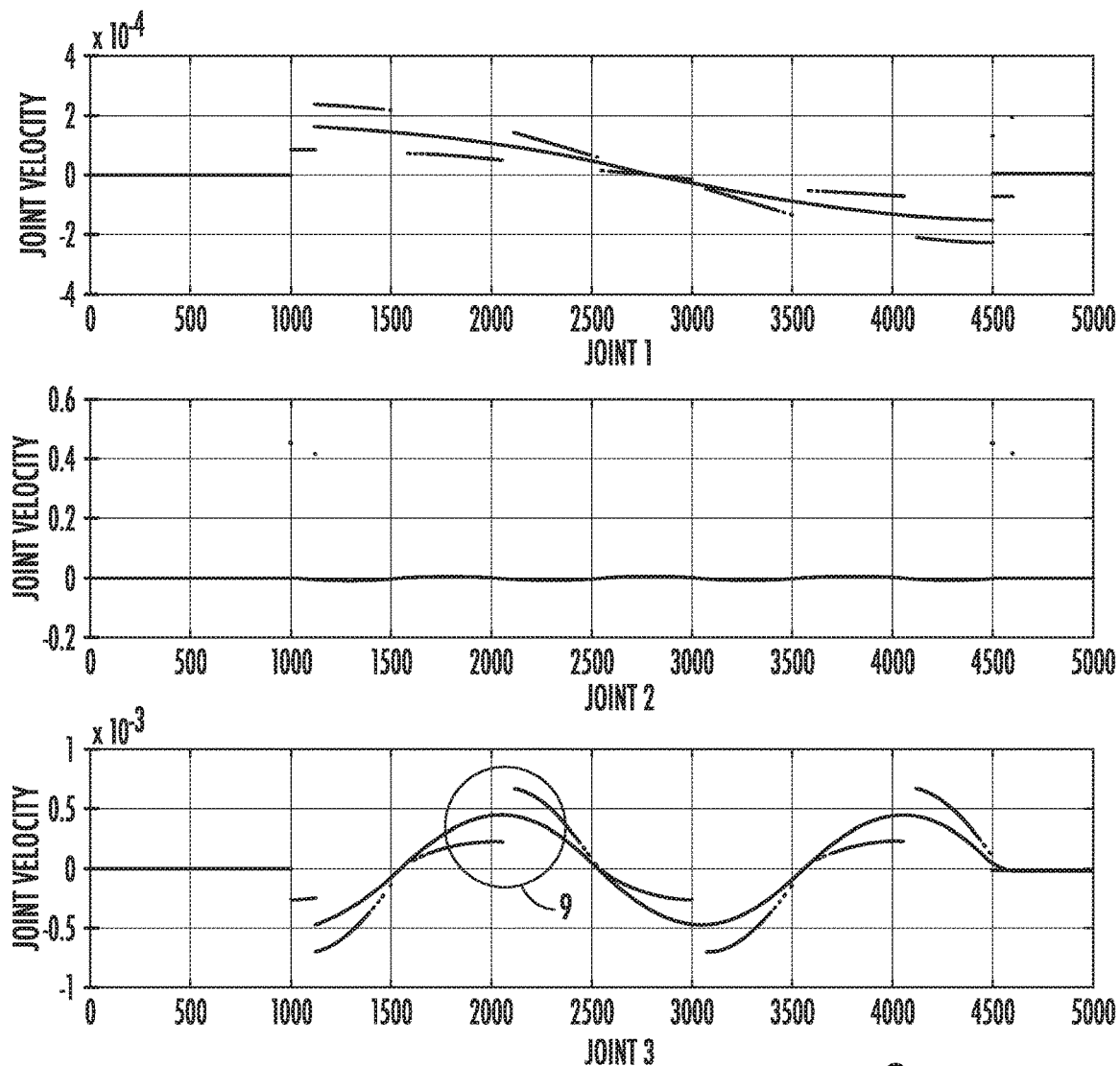
FIG. 8 are graphs of the velocity of the three joints calculated by the velocity based input shaper algorithm of FIG. 7.
Figure 9:
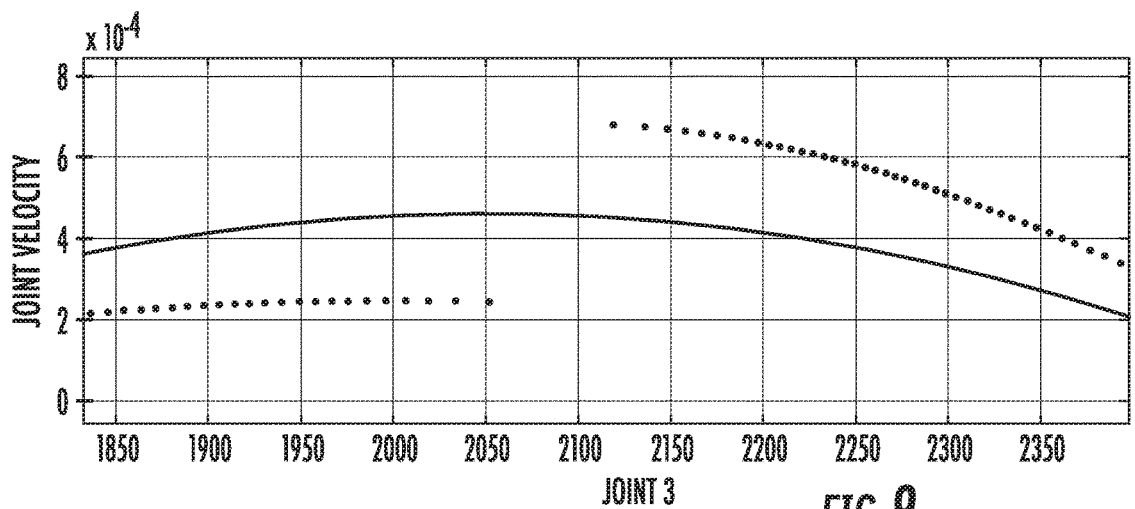
FIG. 9 is an enlarged area of detail of FIG. 8.

Referring to FIG. 8, the velocities computed by the second improved input shaper algorithm to generate the shaped output of FIG. 7 are shown. The double lines indicate that the velocity is discontinuous when the resonant frequency is changing as the linkage 12 moves. For example, when the resonant frequency is increasing, the second set of points is higher when compared to the normal track as a result of the two delayed pulses being added to the undelayed signal. Further, when the resonant frequency is decreasing, the second set of points are lower when compared to the normal track as a result of no delayed pulses being added since the change in resonant frequency causes a change in the delay by more than 1 dt. As shown in FIG. 9, this is more clearly shown by zooming into a portion of the velocity of joint 3 of FIG. 8. The extra points above and below the main curve are a result in the changes of the resonant frequency and flip from below the curve to over the curve as the resonant frequency shifts from decreasing to increasing. It will be appreciated that even though the velocity is not continuous, the shape of the desired position remains smooth as a result of the integration of small values of velocity acts to smooth out the discontinuities. Thus, the smoothness in the desired position is achieved by applying the second improved input shaper algorithm to the desired velocity instead of applying the second improved input shaper algorithm to the desired position.

The implementation of the second improved input shaper algorithm requires the tracking of each delayed pulse and determining when to apply the delayed pulse to the desired signal as the resonant frequency is changing. Below is an example of pseudo code for an embodiment of the second improved input shaper algorithm:

```
function [qOut,Phase,dqRemaining] =
VelocityInputShaper(qIn,qInLast,qOutLast,Phase,dqRemaining)
[NumJoints,BuffSize] = size(Phase);
% Get resonant frequencies for each joint motion based on desired
position
[FreqNow,A] = VibeFrequencyMap4Joints(qIn);
% Calculate change in desired position
dqIn = qIn − qInLast;
% Create vector to store delta phase
dPhase = zeros(Numjoints,1);
% Update phase and delta output buffer
for j = 1:Numjoints
    % Calculate change in phase shift based on current resonant
    frequency
    dPhase(j) = 2*pi*FreqNoW(j)/1000;
    % Shift buffers and add delta phase to all phases in buffer
    for i = BuffSize:−1:2
        Phase(j,i) = Phase(j,i−1) + dPhase(j);
        dqRemaining(j,i) = dqRemaining(j,i−1);
    end;
    % Enter current values as first elements in buffer
    Phase(j,1) = 2*pi*FreqNow(j)/1000;
    dqRemaining(j,1) = (1−A(j))*dqIn(j);
end;
% Set new output equal to previous values to start
qOut = qOutLast;
% Integrate delta outputs into output based on phase information
for j = 1:NumJoints
    % Add current delta input pulse to output
    qOut(j) = qOut(j) + A(j)*dqIn(j);
    % Check if phase is > 180 degrees on delayed pulses
    for i = 1:BuffSize
        if Phase(j,i) >= pi
            % If so, add delayed pulse to desired output signal
            qOut(j) = qOut(j) + dqRemaining(j,i);
            % Set delayed pulse amplitude to zero since it was added
            dqRemaining(j,i) = 0;
        end;
    end;
end;
``` where the servo rate is 1 KHz and the dt is 0.001 seconds. The variables in the above pseudo code are as follows:
qIn—vector of desired joint angles that come in to the input shaper
qInLast—vector of the previous desired joint angles that come in to the input shaper
Phase—array of the phases that have gone by for each of the delayed pulses for each joint
dqRemaining—array of the amplitudes that have yet to be added to the output for each joint
FreqNow—vector of resonant frequencies induced by move for each joint based on current pose
A—vector of % of signal that passes through undelayed for each joint based on current pose
dPhase—vector of change in phase of signal that has gone by since the cycle. This is based on the current resonant frequency and the servo rate, e.g., 1000 Hz
qOutLast—a vector of the previous desired joint angles that come out of the input shaper
qOut—a vector of the calculated desired joint angles that come out of the input shaper.

The second improved input shaper algorithm can be modified to provide smoother velocity signals and integrated position signals by splitting a portion of the delayed dqRemaining by predicting what will happen during the NEXT servo cycle. For example, the second improved input shaper algorithm uses the current phase of each pulse and adds the current dPhase value and verifies if this value is past 180 degrees, or π radians. If the value is greater than 180 degrees, a ratio is computed to determine the amount of phase that goes past 180 degrees compared to the dPhase value. This ratio is saturated to 1 or 0 and is then multiplied by the remaining velocity signal which is then integrated to the desired output signal. This phase look ahead algorithm which includes the ratio and adding the portion of the delayed pulse if the ratio is between 0 and 1 can be implemented with the following pseudo code which can replace the last FOR statement in the pseudo code above such that the phase look ahead algorithm code is as follows:

```
% Integrate delta outputs into output based on phase information
for j = 1:NumJoints
    % Add current delta input pulse to desired output
    qOut(j) = qOut(j) + A(j)*dqIn(j);
    % Check if expected any phase for next cycle will be > 180 degrees
    (pi)
    for i = 1:BuffSize
        if (Phase(j,i) + dPhase(j)) >= pi
            % Calculate ratio of phase that is past pi compared to dPhase
            dPhaseRatio = (Phase(j,i) + dPhase(j) − pi)/dPhase(j);
            % Limit ratio to be between 0 and 1
            dPhaseRatio = min(max(dPhaseRatio,0),1);
            % Add delayed pulse times ratio to desired output signal
            qOut(j) = qOut(j) + dPhaseRatio*dqRemaining(j,i);
            % Decrease delayed pulse amplitude by amount added to output
            dqRemaining(j,i) = (1−dPhaseRatio)*dqRemaining(j,i);
        end;
    end;
end;
```

Figure 10:
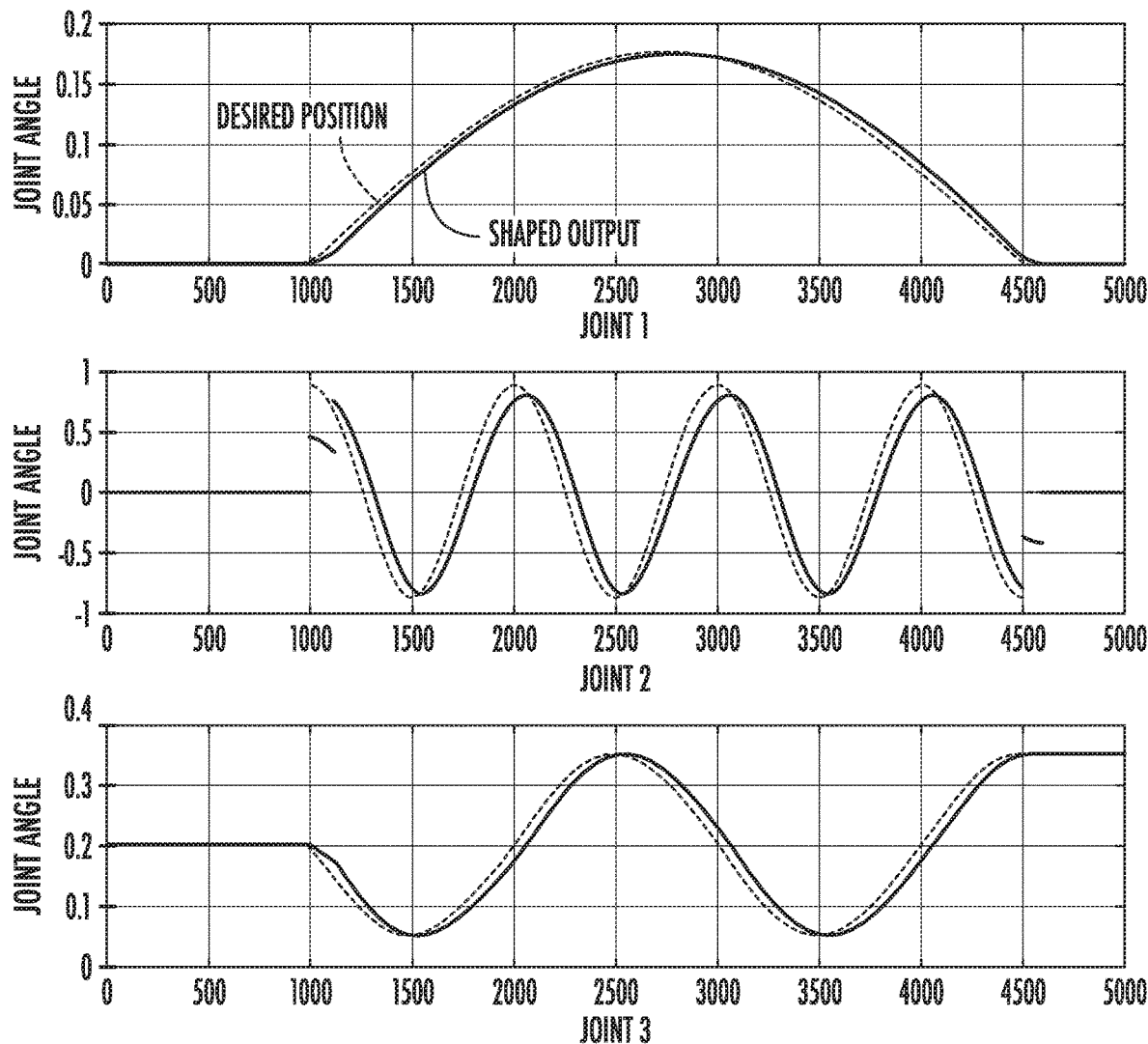
FIG. 10 are graphs of a desired position vs. a shaped position of three joints of the robot base of FIG. 2 when processed through the velocity based input shaper algorithm with a phase look ahead algorithm provided in accordance with the present disclosure.
Figure 11:
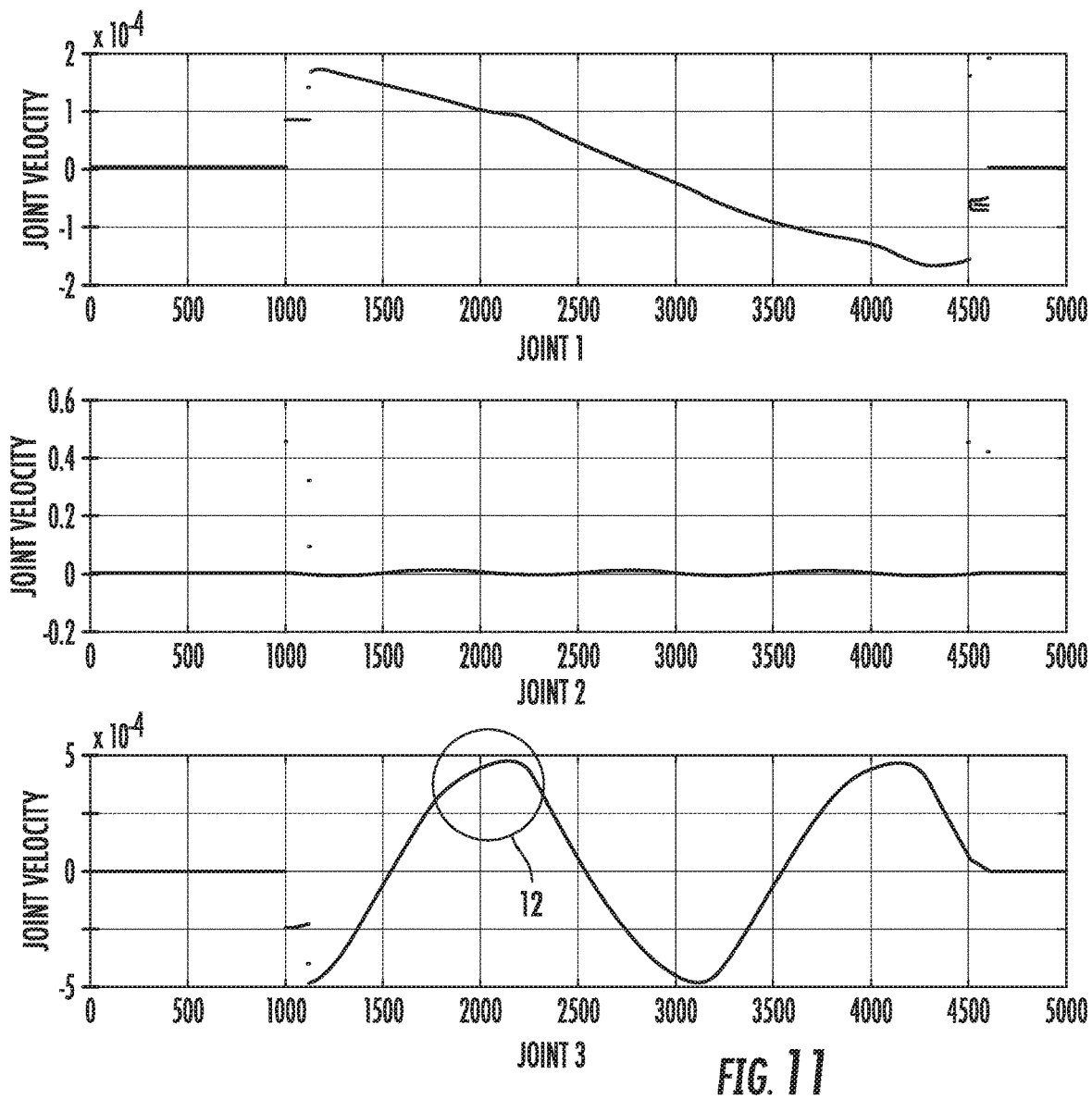
FIG. 11 are graphs of the velocity of the three joints calculated by the velocity based input shaper algorithm of FIG. 10.
Figure 12:
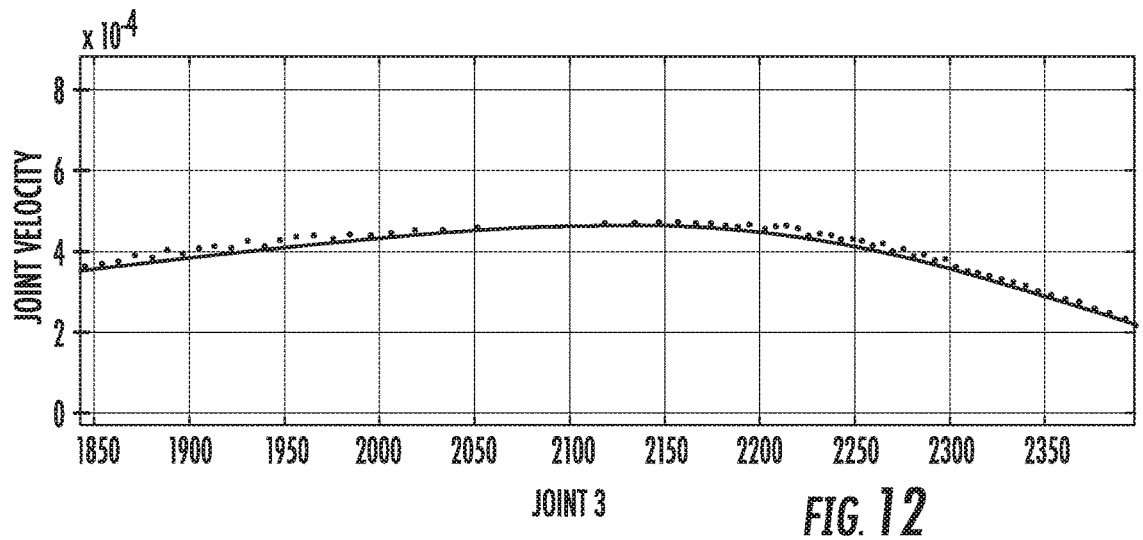
FIG. 12 is an enlarged area of detail of FIG. 11.

As shown in FIGS. 10-12, the phase look ahead algorithm improves the position tracking and velocity tracking when compared to the improved second input shaper algorithm without phase look ahead. Specifically, while the position appears to be similar the smoothness in the velocity is significantly smoothed with a significant decrease in discontinuities in the velocity. In some embodiments, a Kalman filter or another predictive filtering method may be used in addition to or as an alternative to the phase look ahead algorithm detailed above.

A third improved input shaper algorithm in accordance with the present disclosure compensates for a changing resonant frequency in multiple modes. For example, the linkage 12 (FIG. 2) may have a first mode or resonant frequency from a cantilever which vibrates up and down and a second mode or resonant frequency that vibrates side-to-side. The first and second modes may have the same or different resonant frequency. Multiple modes of vibration require an input shaper to suppress multiple modes within a bandwidth of the desired motion.

Figure 13:
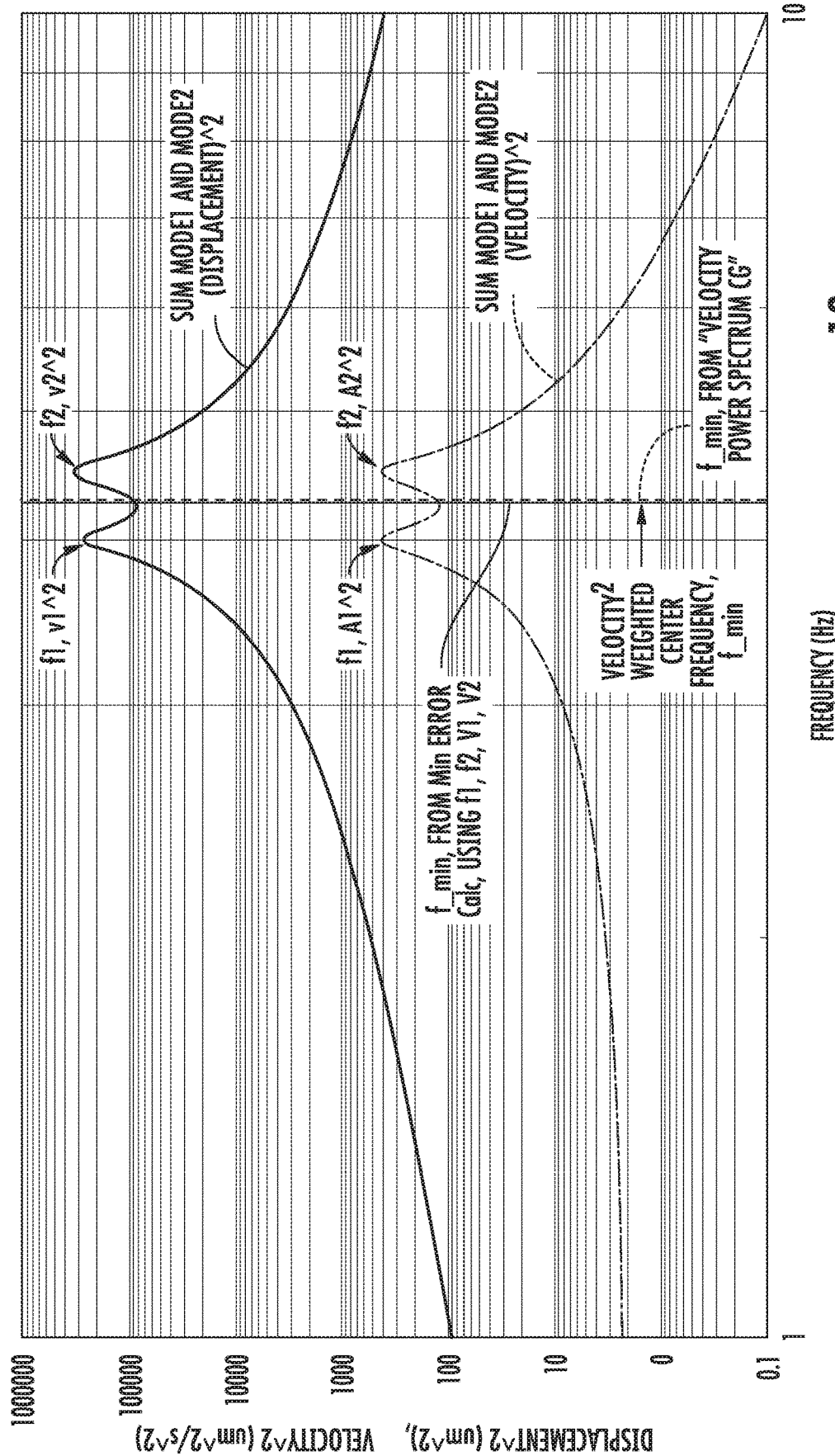
FIG. 13 is a graph illustrating a modal frequency response of a system with two modes of vibration with two distinct resonant frequency peaks.

As shown in FIG. 13, the sum of displacement and velocity of an exemplary structure, e.g., linkage 12, having first and second modes of independent vibration which have a resonant frequency close to one another is shown with a sum of the displacement and velocity of each of the first and second modes in frequency space. The sum in the frequency space is possible for a linear system with independent modes of vibration with the following equation:

$$X_{shaped}(t) = A*X(t) + B*X(t-T_1) + C*X(t-T_2)$$

where A+B+C=1. In the equation above, A is the amount of the signal that is allowed to pass through without delay and B and C are the relative amplitudes that are applied to the first and second modes. The relative amplitude can be determined form the relative height of the displacement peaks, e.g., A1 and A2 in FIG. 13. The values of $T_1$, $T_2$, A, B, and C are all functions of the current robot joint angles and can be determined from a frequency map. Similar to the frequency maps detailed above, the frequency map can be created by putting the structure, e.g., linkage 12, in a known position or pose and pulsing each motor and measuring frequency and amplitude of the resulting vibration in each of the first and second modes at the tool 20 or a center of motion. The frequency map is built by taking these measurements at various points within the workspace of the linkage 12 and creating polynomial expressions or a lookup table such that the frequency map may provide an approximation of the vibration response of movement about each joint across the entire workspace of the linkage 12. An example of pseudo code implementing the third improved input shaper algorithm is as follows:

```
function [qOut,dqBufferNext] =
    InputShaper2Frequency(qIn,qInLast,qOutLast,dqBuffer)
[n,N] = size(dqBuffer);
[T1,T2,A,B,C] = VibeFrequencyMap(qIn);
dqIn = qIn – qInLast;
for i = 1:n
    dqBuffer(i,1) = dqBuffer(i,1) + A(i)*dqIn(i);
    dqBuffer(i,T1) = dqBuffer(i,T1) + B(i)*dqIn(i);
    dqBuffer(i,T2) = dqBuffer(i,T2) + C(i)*dqIn(i);
end;
qOut = qOutLast;
qOut(1:n) = qOut(1:n) + dqBuffer(1:n,1);
dqBufferNext = zeros (n,N);
for i = 1:N-1
    dqBufferNext(1:n,i) = dqBuffer(1:n,i+1);
end;
dqBufferNext(1:n,N) = zeros(n,1);
```

Figure 14:
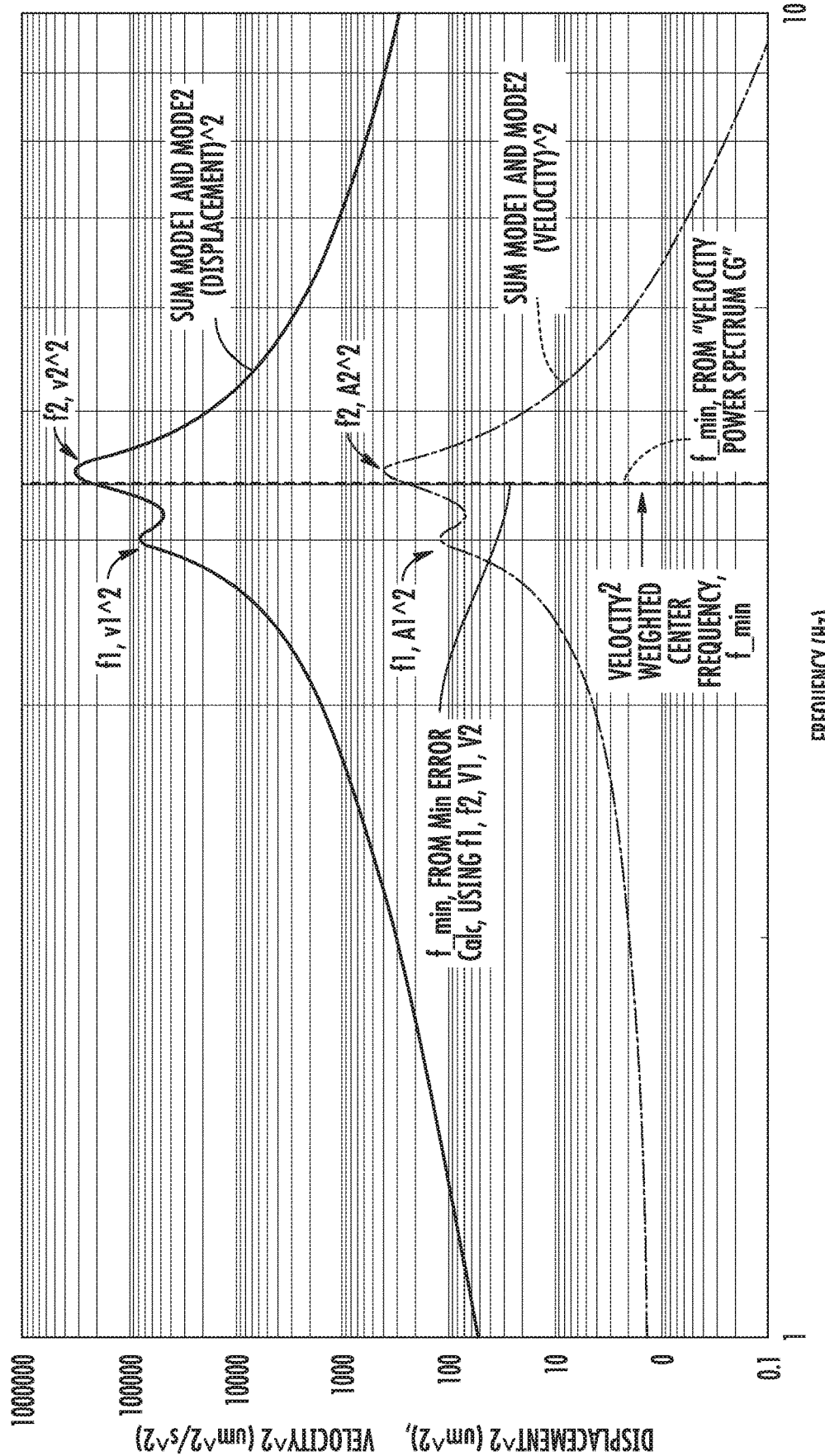
FIG. 14 is a graph illustrating a modal frequency response of a system with two modes of vibration with two resonant frequency peaks close enough that the two resonant frequency peaks begin merge together.
Figure 15:
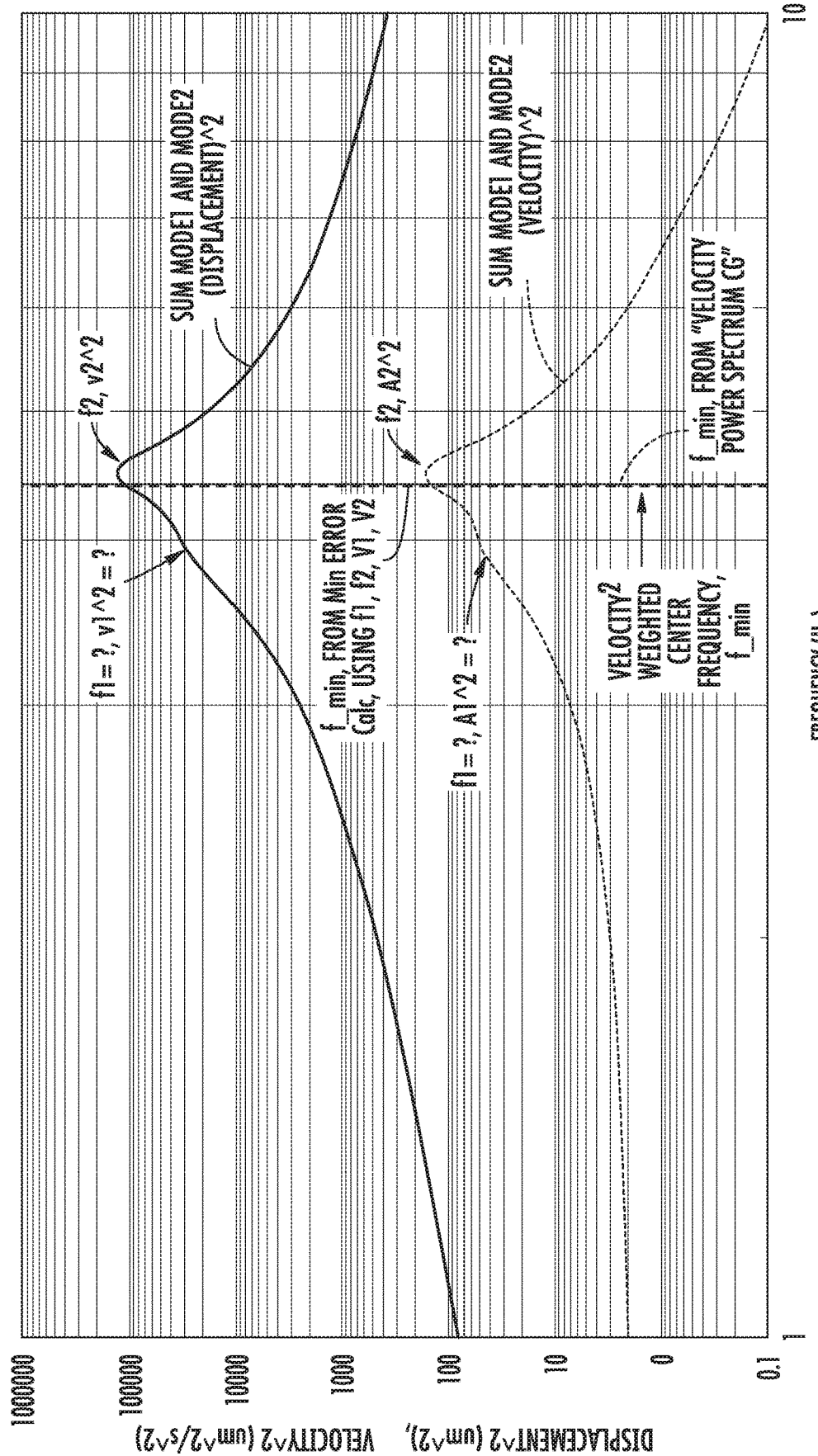
FIG. 15 is a graph illustrating a modal frequency response of a system with two modes of vibration with two resonant frequency peaks close enough that the two resonant frequency peaks merge to a single resonant frequency peak.

While the third improved input shaper algorithm works for most vibration modes, it may be difficult to determine the exact frequency and relative amplitude of the 2 modes when peaks of the modes are close together such that the peaks begin to merge as shown in FIG. 14. In addition, as shown in FIG. 15, the peaks of each mode, A1, A2, are close enough in frequency that the two peaks appear substantially as a single peak.

An alternative method can be used to determine the first moment of the overall shape of the frequency map around the two modes. This fourth improved input shaper algorithm combines the two resonant frequencies of the first and second modes into a single resonant frequency. With reference to FIGS. 13-15, the solid vertical line indicates the best fit of the data using an empirical method while the dotted line shows a frequency calculated by taking the weighted average of the frequency response including the first and second modes. The fourth improved input shaper algorithm may be advantageous by simplifying the calculation of the resonant frequency by merging the two resonant frequencies. In addition, taking the weighted average of the resonant frequencies may minimize noise and/or provide more robust results for varying resonant frequencies as the linkage 12 is moved. Further, a single delayed pulse may be less complex to implement than multiple delayed pulses of the third improved input shaper algorithm.

In embodiments, the third and fourth improved input shaper algorithms may include a look ahead algorithm to further smooth the output velocity as detailed above. While the improved input shaper algorithms detailed above are applied joint space, any of the improved input shaper algorithms may be applied to Cartesian space of a structure, e.g., linkage 12. Applying the improved input shaper algorithms may be advantageous to maintaining a direction of a desired motion.

Figure 16:
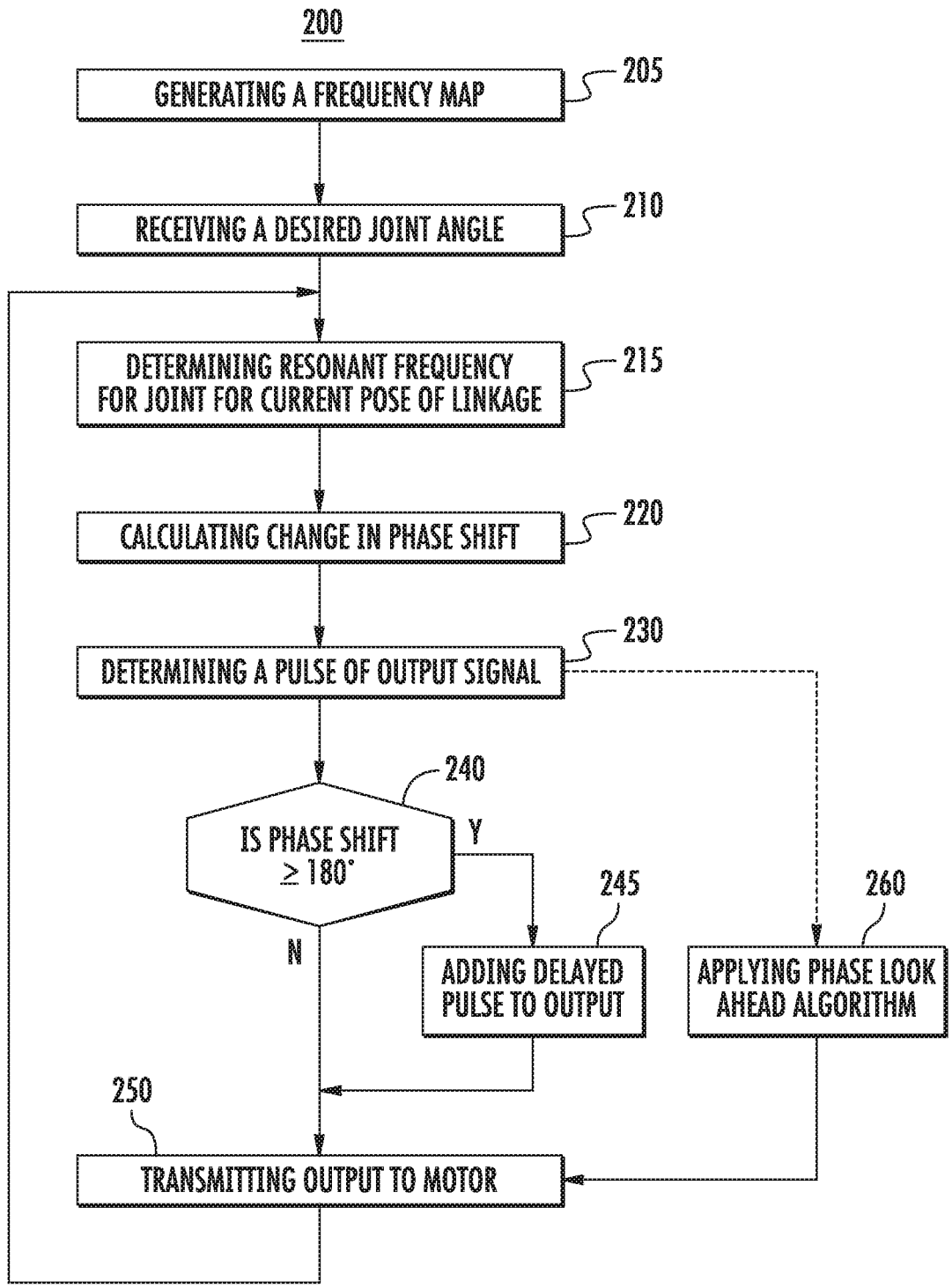
FIG. 16 is a flow chart of an exemplary method of controlling a linkage of a robot.

Referring to FIG. 16, a method 200 of controlling a linkage of a robot is described in accordance with the present disclosure with reference to the robotic surgical system of FIGS. 1 and 2. The method 200 may be carried out by the processing unit 30, the controller 32, 34, and/or the ADU 35. Initially, a frequency map is generated to determine the resonant frequency and/or an overshoot of the linkage 12 is generated for a plurality of poses of the linkage 12 (Step 205). The frequency map may include the resonant frequency and/or the overshoot of for movement about each joint of the linkage 12 (e.g., $J_1$, $J_2$, $J_3$, $J_4$, etc.). In some embodiments, the frequency map includes the resonant frequency and/or the overshoot for multiple modes of vibration of each joint.

During use, the controller (e.g., ADU 35) receives a desired joint angle of one or more joints of the linkage 12 (Step 210). The desired joint angle may be calculated form an input signal including a desired pose of the linkage 12. The desired joint angle may be calculated from forward and/or inverse kinematic models. With the desired joint angle, the resonant frequency and/or overshoot is determined or looked up from the frequency map for each joint of the linkage 12 (Step 215). The resonant frequency and/or overshoot may be calculated as a function of the pose of the current joint angle. With the current resonant frequency, the phase shift is calculated by $2\pi$*current frequency/servo rate (Step 220). The servo rate may be in a range of about 500 Hz to about 2 KHz, e.g., about 1 KHz. With the phase shift, a pulse of an output signal is calculated (Step 230). Next, the phase is checked to determine if the phase is greater than or equal to 180 degrees (Step 240). If the phase is greater than or equal to 180 degrees, a delayed pulse is added to the output signal and the delayed pulse is set to zero (Step 245). If the phase is less than 180 degrees, the delayed pulse is passed through to the next iteration. The output signal is then transmitted to the motor as an output pulse (Step 250) and then the next cycle begins with determining the current resonant frequency and/or overshoot of the joint for the current pose (Step 215).

Figure 17:
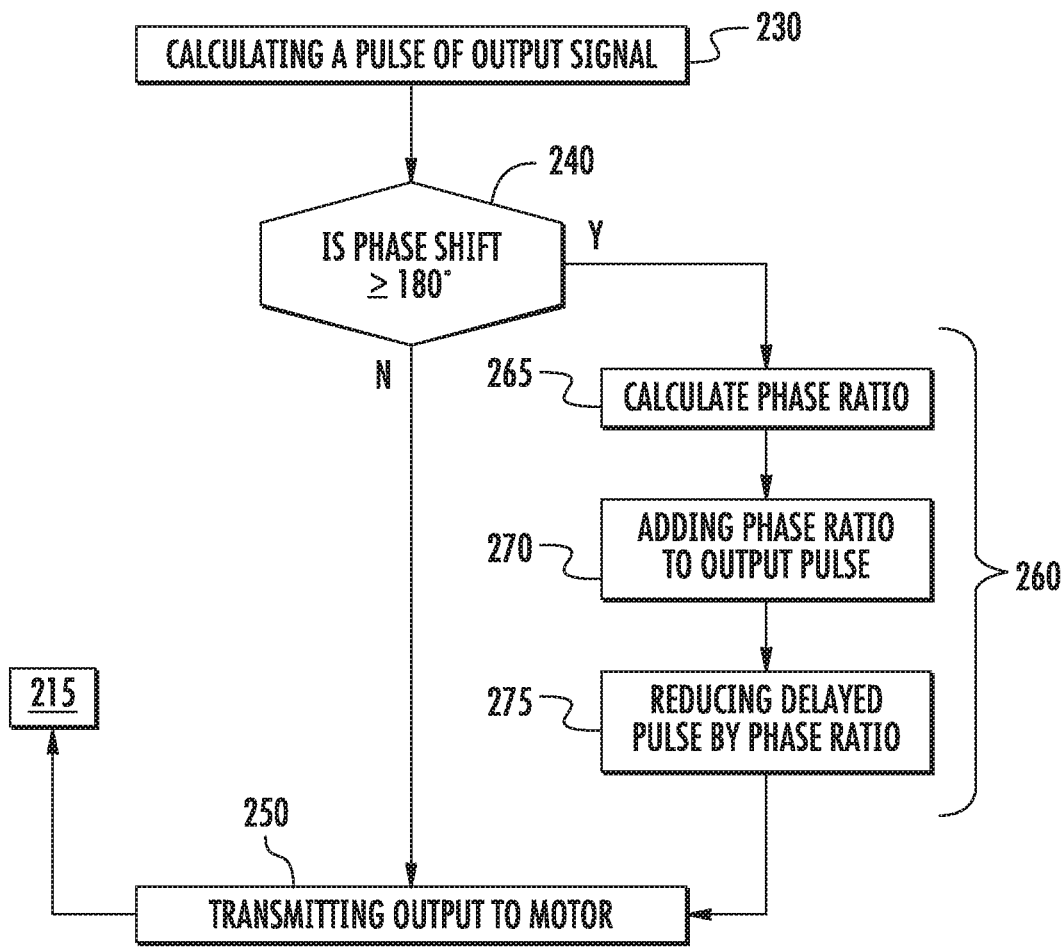
FIG. 17 is a flow chart of an exemplary phase look ahead algorithm.

With additional reference to FIG. 17, the method 200 may include a phase look ahead algorithm 260 to improve position and velocity tracking between step 230 and 250. Specifically, when the phase is greater than or equal to 180 degrees, a phase ratio is calculated which is the amount of the phase being greater than 180 degrees divided by the phase (Step 265). The product of the phase ratio and the delayed signal is added to the output pulse (Step 270) and is subtracted from the delayed signal (Step 275). The output pulse is then transmitted to the motor (Step 250) before the next cycle begins. As shown above in FIGS. 10-12, an input shaper algorithm including such a phase look ahead algorithm may improve position and velocity tracking when compared to the same input shaper algorithm without the phase look ahead algorithm as shown in FIGS. 7-9.

Figure 18:
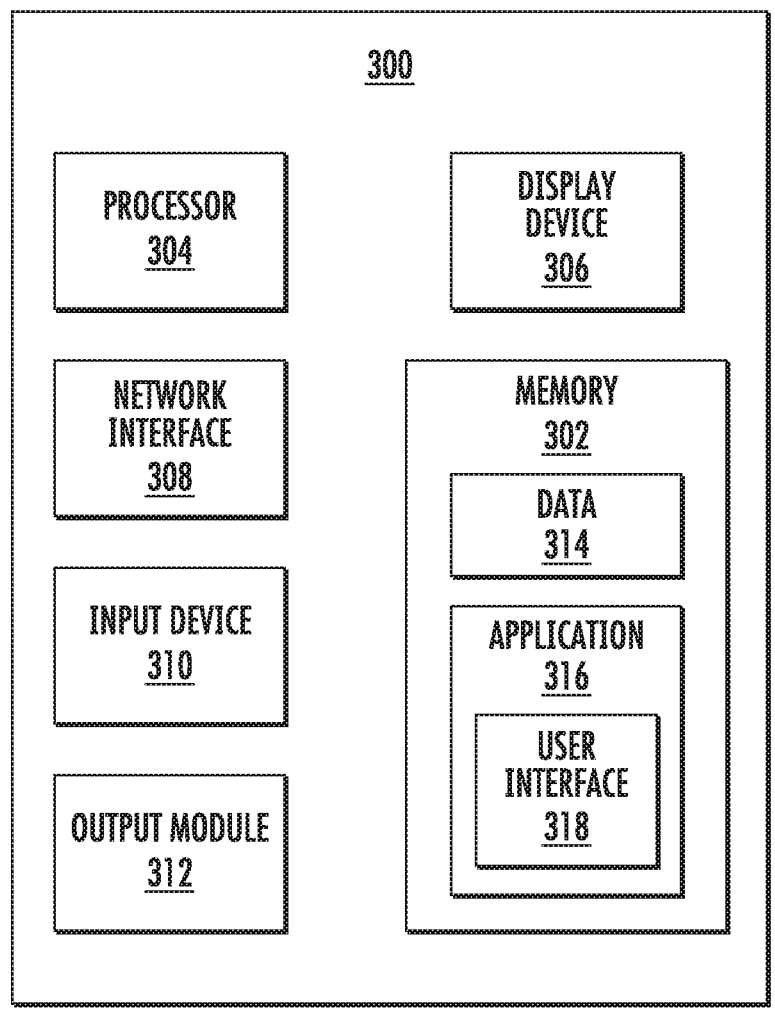
FIG. 18 is a schematic block diagram of an illustrative embodiment of a controller that may be employed in various embodiment of the present system, for instance, as part of the robotic surgical system of FIG. 1.

With reference to FIG. 18, a computing device may be employed in accordance with various embodiments herein. For example, the input shaper algorithms detailed above may be stored in and executed in a computing device. Although not explicitly shown, in some embodiments, the computing device 300, or one or more of the components thereof, may further represent one or more components (e.g., the processing unit 30, the base 18, the controllers 32, 34, the ADU 35, and/or the like) of the robotic surgical system 1. The computing device 300 may, in various embodiments, include one or more memories 302, processors 304, display devices 306, network interfaces 308, input devices 310, and/or output modules 312. The memory 302 includes non-transitory computer-readable storage media for storing data and/or software that is executable by the processor 304 and which controls the operation of the computing device 300. In embodiments, the memory 302 may include one or more solid-state storage devices such as flash memory chips. Alternatively, or in addition to the one or more solid-state storage devices, the memory 302 may include one or more mass storage devices connected to the processor 304 through a mass storage controller (not shown in FIG. 18) and a communications bus (not shown in FIG. 18). Although the description of computer readable media contained herein refers to a solid-state storage, it should be appreciated by those skilled in the art that computer-readable storage media can be any available media that can be accessed by the processor 304. That is, computer readable storage media includes non-transitory, volatile and non-volatile, removable and non-removable media implemented in any method or technology for storage of information such as computer-readable instructions, data structures, program modules or other data. Examples of computer-readable storage media include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 300.

In some embodiments, the memory 302 stores data 314 and/or an application 316. In some aspects the application 316 includes a user interface component 318 that, when executed by the processor 304, causes the display device 306 to present a user interface (not shown in FIG. 18). The network interface 308, in some embodiments, is configured to couple the computing device 300 and/or individual components thereof to a network, such as a wired network, a wireless network, a local area network (LAN), a wide area network (WAN), a wireless mobile network, a Bluetooth network, the Internet, and/or another type of network. The input device 310 may be any device by means of which a user may interact with the computing device 300. Examples of the input device 310 include without limitation a mouse, a keyboard, a touch screen, a voice interface, and/or the like. The output module 312 may, in various embodiments, include any connectivity port or bus, such as, for example, a parallel port, a serial port, a universal serial bus (USB), or any other similar connectivity port known to those skilled in the art.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of controlling a linkage of a robot with a controller, the method comprising:
   receiving a desired joint angle of a joint of the robot;
   transmitting a first control signal to a motor to actuate the joint in response to a desired joint velocity, the desired joint velocity being a function of the desired joint angle and a current joint angle of the joint;
   generating the desired joint velocity by calculating a phase shift of the joint based on a resonant frequency of the joint; and
   upon the phase shift exceeding or equaling 180 degrees, determining a phase ratio, and adding the phase ratio to the first control signal.

2. The method according to claim 1, wherein transmitting the first control signal includes generating the first control signal as a function of a sum of a current joint angle of the joint and a product of the desired joint velocity and a unit of time, wherein the unit of time is a servo rate of the motor.

3. The method according to claim 1, further comprising determining the resonant frequency of the joint based on a current joint angle.

4. The method according to claim 3, wherein determining the resonant frequency of the joint includes calculating the resonant frequency based on a frequency map of the linkage.

5. The method according to claim 1, further comprising transmitting a second control signal to the motor to actuate the joint in response to the desired joint angle, the second control signal including a delayed pulse as a remainder of the desired joint velocity not included in the first control signal.

6. The method according to claim 5, wherein transmitting the second control signal occurs when the phase shift is less than 180 degrees.

7. The method according to claim 1, wherein generating the desired joint velocity includes setting a servo rate of the motor and integrating the desired joint velocity at the servo rate of the motor.

8. The method according to claim 7, further comprising setting the servo rate of the motor in a range of 0.5 KHz to 2 KHz.

9. The method according to claim 1, further comprising generating a frequency map of the linkage before receiving the desired joint angle.

10. The method according to claim 9, wherein the linkage includes a plurality of joints and the frequency map includes a resonant frequency of a first joint and each subsequent joint of the linkage in a plurality of poses of the linkage.

11. The method according to claim 1, wherein the transmitting the first control signal shapes the desired joint velocity in a first mode of vibration.

12. The method according to claim 11, wherein transmitting the first control signal shapes the desired joint velocity in a second mode of vibration.

13. A surgical robot comprising:
a linkage configured to support a tool, the linkage having a joint;
a motor operably coupled to the joint and configured to actuate the joint to vary a joint angle of the joint; and
a controller configured to:
  receive a desired joint angle of the joint;
  transmit a first control signal to the motor to actuate the joint in response to a desired joint velocity, the desired joint velocity being a function of the desired joint angle and a current joint angle of the joint;
  generate the desired joint velocity by calculating a phase shift of the joint based on a resonant frequency of the joint; and
  upon the phase shift exceeding or equaling 180 degrees, determine a phase ratio, and add the phase ratio to the first control signal.

14. The surgical robot according to claim 13, wherein the controller is configured to determine the resonant frequency of the joint based on a current joint angle.

15. The surgical robot according to claim 14, wherein determining the resonant frequency of the joint includes calculating the resonant frequency based on a frequency map of the linkage.

16. A robotic surgical system comprising:
a user interface configured to receive input from a user and to transmit an input signal; and
a surgical robot including:
  a linkage configured to support a tool, the linkage having a joint;
  a motor operably coupled to the joint and configured to actuate the joint to vary a joint angle of the joint; and
  a controller configured to:
    receive the input signal including a desired joint angle of the joint;
    transmit a first control signal to the motor to actuate the joint in response to a desired joint velocity, the desired joint velocity being a function of the desired joint angle and a current joint angle of the joint;
    generate the desired joint velocity by calculating a phase shift of the joint based on a resonant frequency of the joint; and
    upon the phase shift exceeding or equaling 180 degrees, determine a phase ratio, and add the phase ratio to the first control signal.

17. The robotic surgical system according to claim 16, wherein the controller is configured to determine the resonant frequency of the joint based on a current joint angle.

18. The robotic surgical system according to claim 17, wherein determining the resonant frequency of the joint includes calculating the resonant frequency based on a frequency map of the linkage.

* * * * *